United States Patent [19]
Dejaifve et al.

[11] Patent Number: 4,857,498
[45] Date of Patent: Aug. 15, 1989

[54] DEHYDROGENATION CATALYST

[75] Inventors: Pierre E. Dejaifve; Jean-Paul Darnanville; Jacques J. J. Dufour; Roland A. C. Garin, all of Grand Couronne, France

[73] Assignee: Shell Oil Company, Houston, Tex.

[21] Appl. No.: 209,385

[22] Filed: Jun. 21, 1988

[30] Foreign Application Priority Data

Jun. 29, 1987 [FR] France ............... 87 09149

[51] Int. Cl.$^4$ ................. B01J 23/10; B01J 23/78; B01J 23/82
[52] U.S. Cl. ................. 502/304; 502/302; 502/303; 585/444
[58] Field of Search ............ 502/302, 303, 304; 585/444

[56] References Cited

U.S. PATENT DOCUMENTS 3,364,277 1/1968 Siem .................................. 260/680
4,460,709 7/1984 Imanari et al. ..................... 502/304

FOREIGN PATENT DOCUMENTS 0181999 5/1986 European Pat. Off. .
2266738 10/1975 France .
2592375 7/1987 France .

Primary Examiner—W. J. Shine

[57] ABSTRACT 1 to 25% by weight of an alkali metal compound, calculated as stable alkali metal oxide,
0.5 to 20% by weight of a rare earth metal compound, calculated as the oxide,
0.5 to 10% by weight of a calcium compound, calculated as CaO,
0.5 to 10% by weight of a germanium-, tin- and/or lead compound, calculated as the dioxide, and
35 to 97.5% by weight of an iron compound, calculated as $Fe_2O_3$.

9 Claims, No Drawings

DEHYDROGENATION CATALYST

FIELD OF THE INVENTION

The invention relates to a dehydrogenation catalyst suitable for use in the dehydrogenation of hydrocarbons, especially in the dehydrogenation of ethylbenzene to styrene.

BACKGROUND OF THE INVENTION

It is generally known that iron oxide containing catalysts are used in dehydrogenation reactions e.g., the conversion of ethylbenzene into styrene.

A number of catalysts have been described which are based on iron oxide, potassium oxide, together with other promoters such as cerium, chromium, molybdenum and calcium.

In U.S. Pat. No. 4,460,706 issued July 17, 1984, is disclosed a dehydrogenation catalyst mainly based on iron and an alkali metal, a rare earth metal and calcium as promoters, and a process for dehydrogenation making use of the catalyst, e.g., a process for the preparation of styrene. Further prior art has also been discussed in the said U.S. patent application.

SUMMARY OF THE INVENTION

It has now been found that a dehydrogenation catalyst based on iron, alkali metal, rare earth metal and calcium can be further improved by containing an amount of germanium, tin or lead.

The invention accordingly relates to a dehydrogenation catalyst comprising:
1 to 25% by weight of an alkali metal compound, calculated as stable alkali metal oxide,
0.5 to 20% by weight of a rare earth metal compound, calculated as the oxide,
b 0.5 to 10% by weight of a calcium compound, calculated as CaO,
0.5 to 10% by weight of a germanium-, tin- and/or lead compound, calculated as the dioxide, and
35 to 97.5% by weight of an iron compound, calculated as $Fe_2O_3$.

DESCRIPTION OF THE PREFERRED EMBODIMENTS

The selectivity to a certain compound, expressed in a percentage, is defined herein as (a/b)×100 wherein "a" is the amount of alkylbenzene that has been converted into that certain compound and "b" is the total amount of alkylbenzene that has been converted.

The alkali metal compounds which may be used in the process according to the present invention are those of lithium, sodium, potassium, rubidium and cesium. Very good results have been obtained with potassium compounds. The alkali metal compounds are present in the catalyst in an amount of from 1 to 25% by weight, preferably from 5 to 20% by weight, more preferably of from 6 to 15% by weight, calculated as alkali metal oxide. Suitable alkali metal compounds are the oxides, hydroxides and carbonates. Catalysts containing more than 25% by weight of an alkali metal compound have as a disadvantage that their bulk crushing strength is not very high.

The rare earth metals which may be used are lanthanum, cerium, praseodymium, neodymium, promethium, samarium, europium, gadolinium, terbium, dysprosium, holmium, erbium, thulium, ytterbium and lutetium. Mixtures of rare earth metals may be used. Very good results have been obtained with cerium compounds.

The rare earth metal compounds are preferably present in the catalyst in an amount of 1 to 10% by weight, calculated as oxide in the highest valence state on the total catalyst.

It has been found that the presence of a calcium compound provides the extreme high stability of the catalyst being used in the dehydrogenation of hydrocarbons.

The calcium compound is present in an amount of 0.5 to 10% by weight, preferably 0.5 to 5% by weight, calculated as CaO.

The germanium-, tin- or lead compound is present in an amount of from 0.5 to 10% by weight, preferably in an amount of from 0.5 to 5% by weight, more preferably in an amount of from 0.8 to 4% by weight of the total catalyst and calculated on the dioxide.

An attractive feature is that the present catalyst does not need to contain molybdenum, but, if desired, molybdenum may be present.

The dehydrogenation process is suitably carried out using a molar ratio stream to alkylbenzene in the range of from 2 to 20 and preferably of from 5 to 13. Another attractive feature is that relatively low molar ratios steam to alkylbenzene can be used.

The dehydrogenation processes are suitably carried out at a temperature in the range of from 500° C. to 700° C. An attractive feature of the process is that relatively low temperatures can be used, particularly in the range of from 550° C. to 625° C.

The dehydrogenation processes may be carried out at atmospheric or super- or subatmospheric pressure. Atmospheric pressure and pressures between 1 bar and 0.5 bar absolute are usually very suitable.

The dehydrogenation processes are suitably carried out using a liquid hourly space velocity in the range of from 0.1 to 5.0 liter of alkylbenzene per liter of catalyst per h, using, for example, a tubular or radial flow reactor.

An alkylbenzene may be used as a starting compound in the dehydrogenation process and has suitably 2 or 3 carbon atoms in the alkyl group. Very good results have been obtained with ethylbenzene. Isopropylbenzene is another example of a starting compound. If desired, the aromatic nucleus in the alkyl benzene may carry a second substituent, for example a methyl group.

The catalyst may be used in the form of, for example, pellets, tablets, spheres, pills, saddles, trilobes or tetralobes.

The iron oxide to be used for the preparation of the novel catalysts may be, for example, hydrated or not-hydrated $Fe_2O_3$. The iron oxide may be a synthetically produced, powdered red, red-brown, yellow or black pigment. The red or red-brown pigments are highly pure ferric oxide, while the black pigment is the magnetic form, ferrosoferric oxide ($Fe_3O_4$), which is usually found in the catalyst under various reaction conditions. The yellow iron oxides consist of the monohydrated form of ferric oxide. These oxides are prepared by various methods, for example oxidation of iron compounds, roasting, precipitation, calcination, and the like. A suitable form of iron compound is the mono-hydrated yellow iron oxide used in the preparation of catalysts according to U.S. Pat. Specifications Nos. 3,360,597 and 3,364,277 incorporated by reference herein. Particularly, suitable are pigment grade red iron oxides of purities exceeding 98% by weight. These red oxies have surface areas ranging from 2 to 50 m$^2$/g. The alkali metal compound, the rare earth metal compound, e.g., cerium compound, calcium compound and tin compound may be brought onto the iron oxide in any suitable manner, for example by intimately mixing iron oxide with a suitable alkali metal compound, a suitable cerium compound, a suitable calcium compound and a suitable tin compound in the presence of water. The mixture obtained may be dried and then calcined at a temperature in the range of from, for example, 500° C. to 1200° C.

Suitable alkali metal compounds are, for example, carbonates, hydrogen carbonates, nitrates and acetates; suitable cerium compounds are, for example, cerium nitrate, cerium carbonate and cerium acetate; suitable calcium compounds are calcium nitrate, calcium carbonate, calcium acetate and calcium isobutyrate.

Suitable germanium-, tin- or lead compounds are, for example, sulfates, nitrates, carbonates, acetates and oxides of these metals. Also stannates, germanates and plumbates are suitable.

Catalysts having a highly porous structure and a low surface area are highly active in catalytic dehydrogenation. Various methods may be employed to form highly porous catalysts. For example, combustible materials, such as sawdust, carbon, wood flour, etc., may be added during catalyst formation, and then burned out after the pellet has been formed. Many of these porosity-promoting aids also assist in facilitating extrusion of pellets, for example, the use of graphite, potassium alginate and aqueous solutions of methyl cellulose.

If desired, the catalyst may be used supported on a carrier, for example zinc aluminate.

The ranges and limitations provided in the instant specification and claims are those which are believed to particularly point out and distinctly claim the instant invention. It is, however, understood that other ranges and limitations that perform substantially the same function in substantially the same manner to obtain the same or substantially the same results are intended to be within the scope of the instant invention as defined by the instant specification and claims.

The following example further illustrates the invention and is not intended to limit the scope thereof.

EXAMPLE 1

A dehydrogenation catalyst containing 79.6% wt Fe$_2$O$_3$, 11% wt K$_2$O, 6.8% wt CeO$_2$, 1.2% wt SnO$_2$ and 1.4% wt CaO, was prepared as follows. An intimate mixture was prepared starting from red iron oxide (unhydrated), potassium carbonate, cerium carbonate, tin dioxide, calcium carbonate and potassium alginate with gradual addition of water during mixing. The paste obtained was extruded and pelletized to cylindrical particles having a diameter of 3 mm and a length of 5 mm. The cylinders were dried for 2 h at 75° C. and 3 h at 110° C. and then calcined for 2 h at 800° C. and then allowed to adopt ambient temperature.

A mixture of ethylbenzene and steam heated to a certain temperature, was introduced into a reactor and lead over 100 ml of catalyst, prepared as described above.

The mixture was conducted at a certain pressure and a certain liquid hourly space velocity through the catalyst bed.

The temperature was adjusted so that the conversion of ethylbenzene was 70%. The reaction product leaving the reactor was analyzed by means of gas-liquid chromatography. For the data obtained the temperature at 70% ethylbenzene conversion and the selectivity to styrene was calculated.

The steam to ethylbenzene molar ratios were different in the experiments, viz. 12, 8 and 6.5. The temperature ($T_7$) of the catalyst was adjusted until the conversion of ethylbenzene was 70%. The selectivity to styrene at 70% conversion is indicated as $S_{70}$.

The stability of the catalysts was determined at a molar ratio steam to ethylbenzene of 6.5 by determining the average increase of the temperature which was necessary to keep the conversion of ethylbenzene at the constant value in each experiment. This average increase of temperature is indicated as "°C./day".

In the table the $T_{70}$- and $S_{70}$-values are given.

EXAMPLE (COMPARATIVE)

A dehydrogenation catalyst was prepared as described in Example 1, with the exception that no SnO$_2$ was added and the amount of other promoters remained the same. This catalyst was used as in Example 1 described. The results are given in the table.

TABLE

| | pressure steam/ethylbenzene | | pressure steam/ethylbenzene | | 575° C. steam/ethylbenzene |
|---|---|---|---|---|---|
| | 1 bar | mol ratio 12 | 0.75 bar | mol ratio 8 | mol ratio 6.5 |
| Example | $T_{70}$ | $S_{70}$ | $T_{70}$ | $S_{70}$ | °C./day |
| 1 | 611° C. | 94.1 | 610° C. | 95.5 | 2.3 |
| COMPARATIVE | 609° C. | 93.1 | 603° C. | 94.2 | 2.2 |

LHSV = 0.65 h$^{-1}$

We claim:
1. A dehydrogenation catalyst comprising:
   1 to 25% by weight of an alkali metal compound, calculated as stable alkali metal oxide,
   0.5 to 20% by weight of a rare earth metal compound, calculated as the oxide,
   0.5 to 10% by weight of a calcium compound, calculated as CaO,
   0.5 to 10% by weight of a germanium-, tin- and/or lead compound, calculated as the dioxide, and
   35 to 97.5% by weight of an iron compound, calculated as Fe$_2$O$_3$.
2. Dehydrogenation catalyst as claimed in claim 1, wherein the alkali metal compound is a potassium compound.
3. Dehydrogenation catalyst as claimed in claim 1 or 2, wherein the rare earth metal is cerium.
4. Dehydrogenation catalyst as claimed in claim 1 or 2, wherein the amount of rare earth metal compound lies in the range of from 1 to 10% by weight.
5. Dehydrogenation catalyst as claimed in claim 1 or 2, wherein the amount of alkali metal compound lies in the range of from 6 to 15% by weight.

6. Dehydrogenation catalyst as claimed in claim 1 or 2, wherein the amount of calcium compound lies in the range of from 0.5 to 5% by weight.

7. Dehydrogenation catalyst as claimed in claim 1 or 2, wherein the amount of tin compound lies in the range of from 0.5 to 5% by weight.

8. Dehydrogenation catalyst as claimed in claim 7, wherein the amount of tin compound lies in the range of from 0.8 to 4% by weight.

9. A dehydrogenation catalyst comprising:

6 to 15% by weight of a potassium compound, calculated as potassium oxide ($K_2O$), 1 to 10% by weight of a cerium compound, calculated as cerium oxide ($CeO_2$), 0.5 to 5% by weight of a calcium compound, calculated as calcium oxide (CaO).

0.5 to 5% by weight of tin compound calculated as tin oxide($SnO_2$) and 65 to 92% by weight of an iron compound, calculated as $Fe_2O_3$.

* * * * *